United States Patent [19]

Horwath et al.

[11] 4,447,531

[45] May 8, 1984

[54] GLUCOSE ISOMERASE FROM FUNGI OF THE BASIDIOMYCETES CLASS

[75] Inventors: Robert O. Horwath, Westport; Robert M. Irbe, Norwalk, both of Conn.

[73] Assignee: Nabisco Brands, Inc., Parsippany, N.J.

[21] Appl. No.: 393,849

[22] Filed: Jun. 30, 1982

[51] Int. Cl.$^3$ .................. C12P 19/24; C12P 19/20; C12R 1/645
[52] U.S. Cl. ................................ 435/94; 435/234; 435/911
[58] Field of Search ..................... 435/94, 234

[56] References Cited

U.S. PATENT DOCUMENTS 4,308,349  12/1981  Foley et al. .................. 435/234

OTHER PUBLICATIONS

Chemical Abstracts, vol. 96, 1982, 17343m (abstract of New Phytol, 1981, 89(3) 419–428 (Hammond).
Enzyme Nomenclature, 1978 (published 1979), pp. 418–421.

*Primary Examiner*—Lionel M. Shapiro
*Attorney, Agent, or Firm*—R. Kornutik

[57] ABSTRACT

Glucose isomerase is produced by cultivating fungi of the Basidiomycetes class and is used for isomerizing glucose to fructose.

13 Claims, No Drawings

GLUCOSE ISOMERASE FROM FUNGI OF THE BASIDIOMYCETES CLASS

BACKGROUND OF THE INVENTION

This invention relates to enzymatic processes for converting glucose (dextrose) to fructose (levulose).

Most food grade glucose is provided as an enzymatic hydrolysate of corn starch, i.e., the corn syrup of commerce. Glucose is generally rated as being 60 to 80% as sweet as sucrose and therefore sells at a correspondingly lower price. It has long been known to isomerize glucose to fructose which is even sweeter than sucrose by employing an enzyme having glucose isomerase activity, preferably one which has been immobilized by adsorption onto insoluble supports, such as crosslinking the enzyme with the support matrix and entrapment in a polymer matrix support such as diethylaminoethylcellulose or porous glass. The isomerization of glucose provides an equilibrium mixture typically containing 42–50% fructose and is referred to as high fructose corn syrup (HFCS).

It is known that glucose isomerase can be isolated from a substantial number of microorganisms including species of Streptomyces, Bacillus, Arthrobacter, Nocardia, Lactobacillus, Ampullariella, and various other genera of microorganisms, and the enzyme has been employed in the commercial production of fructose from glucose by known isomerization techniques to provide mixtures of glucose and fructose. In the commercial process most commonly in present use, cornstarch is liquefied, enzymatically or chemically, and then treated with glucoamylase to produce glucose which is thereafter isomerized using glucose isomerase to mixtures containing both fructose and glucose. Higher concentrations of fructose are particularly desirable and may be obtained by the use of more active enzymes and/or the use of high isomerization temperatures.

Detailed descriptions of the enzymatic conversion of glucose to fructose employing glucose isomerase can be found in Hamilton, et al. "Glucose Isomerase: A Case Study of Enzyme-Catalyzed Process Technology", *Immobilized Enzymes in Food and Microbial Processes*, Olson et al., Plenum Press, New York, (1974), pp. 94–106, 112, 115–137; Chen, et al., "Glucose Isomerase (a Review)", *Process Biochem.*, (1980), pp. 30–35; Chen, et al., "Glucose Isomerase (a Review)", *Process Biochem.*, (1980), pp. 36–41; Nordahl, et al., "Fructose Manufacture from Glucose by Immobilized Glucose Isomerase", *Chem. Abstracts*, vol. 82, (1975), Abs. No. 110316h; and, Takasaki, "Fructose Production by Glucose Isomerase", *Chem. Abstracts*, vol. 81, (1974), Abs. No. 76474a. In addition, there are numerous patents relating to glucose isomerization of which U.S. Pat. Nos. 3,616,221; 3,623,953 (Reissue 28,885); 3,964,313; 3,708,397; 3,715,276; 3,788,945; 3,909,354; 3,960,663; and, 4,308,349 are representative.

Because of the economics involved in producing glucose isomerase, it is of the utmost importance to use the isomerase under conditions whereby maximum yields of fructose are produced using minimum quantities of glucose isomerase. Moreover, the conditions for isomerization should be such that minimal quantities of objectionable by-products are produced.

SUMMARY OF THE INVENTION

It has now been surprisingly discovered that fungi of the class Basidiomycetes produce significant quantities of glucose isomerase. In particular, species of Flammulina, Phellinus, Irpex, Mucronella, Stereum, Perenniporia, Ramaricium, Sebacina, Lentinus, Coriolus and Pannelus accumulate isomerase activity which is produced in the mycelia of these organisms. The glucose isomerase can be separated from the mycelia by the usual extraction techniques e.g. using sonic treatment or chemical lysing or alternatively the mycelia can be used directly.

In addition to the aforementioned microorganisms, the present invention contemplates the use of mutants and variants thereof as well as genetically transformed microorganisms derived therefrom by introduction of the respective glucose isomerase genes into other microorganisms including mesophilic and preferably thermophilic microorganisms. Of particular importance are those genetically transformed microorganisms produced by introduction of mutated glucose isomerase genes into preferably thermophilic microorganisms. The mutated glucose isomerase genes selected for such use are those which provide glucose isomerase which is stable at elevated temperatures, especially above 90° C. and preferably up to about 110° C. Such genes can be prepared by the usual techniques used for mutation of microorganisms such as irradiation or chemical means. Thus, isolated glucose isomerase genes which produce glucose isomerase of moderate thermal stability, on in vitro mutagenesis will undergo mutation, and selection of the appropriate mutated genes is accomplished by reintroduction of the mutated gene into either the parent or other organism, preferably a thermophilic organism followed by replication of the organism and testing of the thermal stability of the resulting glucose isomerase.

DESCRIPTION OF THE PREFERRED EMBODIMENTS

The glucose which is isomerized to fructose in accordance with the present invention can be derived from any of the known sources for this sugar. For reasons of economy, the glucose will usually be derived from the hydrolysis of starch or cellulose employing acid and/or enzyme, preferably the latter, in accordance with known procedures. Glucose obtained in this way will typically contain minor quantities of polysaccharides, sugar oligomers, etc., depending upon the carbohydrate source employed and the hydrolysis method utilized. Cereal grains such as corn, milo, wheat, rye, and the like, and amylaceous roots and tubers such as potatoes, yams, carrots, cassava (manioc), and the like, are excellent sources of starch for conversion to the glucose starting material of this invention. In the United States, corn starch is especially preferred due to its comparatively low cost and ready availability. Since the production of food grade glucose favors the use of enzymatic starch hydrolysis procedures, such procedures are preferred herein. Enzyme hydrolysis methods are described in U.S. Pat. Nos. 4,017,363, 3,912,590; 3,922,196, 3,922,197–201 and 4,284,722, the disclosures of which are incorporated by reference herein. Glucose can be isomerized to fructose in accordance with the present invention employing any of the known procedures, including contacting glucose solutions with whole cells, or passing the solutions through a bed containing bound, or immobilized, glucose isomerase. Materials and procedures used for the immobilization of enzymes are well known and are described in a number of publications including Wang, et al., *Fermentation & Enzyme Technology*, John Wiley & Sons, Inc., New York (1979), pp. 318—318 and Kirk-Othmer, *Encyclopedia of Chemical Technology*, 3rd Ed., John Wiley & Sons, Inc., New York, (1980) Vol. 9, pp. 148-172, the disclosures of which are incorporated by reference herein.

Particularly preferred species of the aforesaid glucose isomerase producing Basidiomycetes for use in the present invention include:

| Fungus | ATCC Number |
| --- | --- |
| *Stereum striatum* | 20633 |
| *Irpex mollis* | 20634 |
| *Lentinus edodes* | 20635 |
| *Perenniporia compacta* | 20636 |
| *Ramaricium albofdanescens* | 20637 |
| *Sebacina calcea* | 20638 |
| *Coriolus versicolor* | 20639 |
| *Panellus stipticus* | 20640 |
| *Mucronella aggregata* | 20641 |
| *Flammulina velutipes* | 20642 |
| *Phellinus torulosus* | 20632 |

Cultures of strains of these preferred species of fungi have been deposited with the American Type Culture Collection where these organisms were accorded the indicated accession numbers, i.e. ATCC number.

The determination of other glucose-isomerase-producing fungi of the Basidiomycetes class can be carried out using a simple test procedure. Cultures of the test organism are incubated for 7 days at 25° C. with vigorous shaking in a growth medium containing cornsteep liquor, magnesium sulfate, potassium phosphate, xylose and agar in shake flasks. These cultures are then checked for glucose isomerase activity using fructose determination methods, such as the acid carbazol-cysteine test, or xylulose determination methods, using gas chromatography or high pressure liquid chromatography (HPLC).

Using these test procedures, or obvious modifications thereof, various species of fungi can be tested to determine the presence of the desired glucose isomerase activity.

The selected fungi can be grown in accordance with known methods of propagation. One such method employs xylose as carbohydrate source as well as other ingredients usually present in such media such as cornsteep liquor, inorganic salts and the like.

After growth for a sufficient period of time, e.g. to about 120 hours, the mycelia are harvested usually by filtration followed by washing with water buffered to a pH in the range of 6 to 7. The enzyme is then extracted by known physical or chemical procedures, such as using sonication, cell homogenization, lytic enzymes, surfactants, etc. The extract may be passed through a Sephadex column (G-25) for purification. The enzyme extract can now be used in the isomerization reaction. Alternatively, as previously mentioned, the mycelia can be used as the source of the enzyme in the isomerization mixture.

In order to describe more clearly the nature of the present invention, a specific example will hereinafter be described. It should be understood, however, that this is done solely by way of example and is intended neither to delineate the scope of the invention nor limit the ambit of the appended claims.

EXAMPLE

Preparation of glucose isomerase

*Mucronella aggregata* ATCC 20641 was grown in accordance with the following procedure:

A. Culture Maintenance: After incubating the cultures on malt agar slants for 7 days at 30° C., the isolates were inoculated into shaker flasks or maintained under refrigeration (about 10° C.).

B. Shake Flask Propagation: Inoculation medium was made up as follows:

| Ingredient | % By Weight |
| --- | --- |
| Cornsteep liquor | 2.0 (d.b.) |
| Xylose | 5.0 |
| $KH_2PO_4$ | 0.1 |
| $MgSO_4.7H_2O$ | 0.15 |
| Agar | 0.4 |
| adjust pH to 6.5 | |

80 Ml aliquots of the above medium were placed in 500 ml Erlenmyer flasks together with 20 ml of a 25% glucose solution (sterilized) for the inoclum fermentation. Production flasks ere similarly charged except no agar was added.

First Stage (test tube) Propagation

In a sterile hood, approximately one half of the mycelia from a slant is transferred with a metal loop to a test tube with 10 ml of the inoculation medium and about six 3-mm glass beads (sterile). The tubes are vortexed for 30-60 seconds or until the mycelia are dispersed. The tubes are then placed on a G-50 shaker at 200 rpm, 30° C., for 7 days.

Second stage (inoculum) Propagation

After 7 days, 5 ml are transferred to a 500 ml Erlenmeyer shake flask, and 1 ml is transferred into brain heart infusion to check sterility. These inoculation flasks are placed on a G-50 shaker at 200 rpm, 30° C., for 7 days.

Third stage (production) Propagation

After 7 days, 5 ml are transferred from the inoculation flask to several fermentation flasks. The fermentation flasks are placed on the G-50 shaker at 200 rpm, 30° C., for 9 days.

C. Harvesting Cell Biomass

After the 9-day incubation period, the pH of each shake flask was measured; the cell biomass was filtered and washed twice with pH 7.0 phosphate buffer. After the second filtration, the harvested cell biomass from each culture was weighed and frozen for bioconversion experiments.

Cell-Free Extract Preparation

Mycelia (4 g. wet weight) in phosphate buffer (pH 6.5) are blended in a Waring blender at low speed for 15 seconds. The buffered homogenate is then transferred to a 50 ml. glass Duran Sample Flask containing 50 g. (about 80% by volume) glass beads of a diameter of 0.45 to 0.5 mm. The chamber is then vigorously agitated with a Braun Mechanical Cell for 1 minute while cold carbon dioxide is allowed to flow past the chamber to minimize heating.

Alternatively, the low speed blended mycelia in buffer is placed in a plastic centrifuge tube in an ice bath and then sonicated with a Heat Systems Ultrasonics Cell Disrupter, Model 350, set at 50% duty cycle, output control at 6, continuous mode, in 5 cycles of 15 seconds on and 15 seconds off.

Isomerization of glucose to fructose

The isomerization mixture containing 10% by weight glucose (maleate-buffered to pH 6.7), $MgCl_2$ (10 mM), $Co^{+2}$ (1 mM) and enzyme solution (50 mg of protein) was incubated at 60° C. for 3 hours.

Assay of the mixture, actually aliquots thereof, showed the presence of fructose in addition to glucose. The assays employed were gas chromatography and the cysteine carbazole method (N. E. Lloyd, Cereal Chem., 49, #5, pp. 544–553, 1972).

We claim:

1. A process for preparing fructose which comprises contacting an aqueous solution of glucose with glucose isomerase produced by at least one species of the Basidiomycetes class of fungi to convert at least a portion of said glucose to fructose.

2. The process of claim 1 wherein said species is a species of the genera Stereum, Irpex, Lentinus, Perenniporia, Ramaricium, Sebacina, Coriolus, Panellus, Mucronella, Flammulina, and Phellinus.

3. The process of claim 2 wherein the species is *Stereum striatum*.

4. The process of claim 2 wherein the species is *Irpex mollis*.

5. The process of claim 2 wherein the species is *Lentinus edodes*.

6. The process of claim 2 wherein the species is *Perenniporia compacta*.

7. The process of claim 2 wherein the species is *Ramaricium albofdanescens*.

8. The process of claim 2 wherein the species is *Sebacina calcea*.

9. The process of claim 2 wherein the species is *Coriolus versicolor*.

10. The process of claim 2 wherein the species is *Panellus stipticus*.

11. The process of claim 2 wherein the species is *Mucronella aggregata*.

12. The process of claim 2 wherein the species is *Flammulina velutipes*.

13. The process of claim 2 wherein the species is *Phellinus torulosus*.

* * * * *